(12) United States Patent
Subramaniam et al.

(10) Patent No.: US 10,730,814 B2
(45) Date of Patent: Aug. 4, 2020

(54) OZONE-FACILITATED SELECTIVE OXIDATION OF ALKANES IN LIQUID CARBON DIOXIDE (71) Applicant: University of Kansas, Lawrence, KS (US)

(72) Inventors: Bala Subramaniam, Lawrence, KS (US); Andrew M. Danby, Lawrence, KS (US); Michael D. Lundin, Lawrence, KS (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 16/324,163

(22) PCT Filed: Aug. 10, 2017

(86) PCT No.: PCT/US2017/046258
§ 371 (c)(1),
(2) Date: Feb. 8, 2019

(87) PCT Pub. No.: WO2018/031749
PCT Pub. Date: Feb. 15, 2018

(65) Prior Publication Data
US 2019/0177254 A1 Jun. 13, 2019

Related U.S. Application Data (60) Provisional application No. 62/373,397, filed on Aug. 11, 2016, provisional application No. 62/408,863, filed on Oct. 17, 2016.

(51) Int. Cl.
*C07C 45/40* (2006.01)
*C07C 27/12* (2006.01)
*C07C 27/16* (2006.01)
*C07C 29/48* (2006.01)

(52) U.S. Cl.
CPC ............. *C07C 27/12* (2013.01); *C07C 27/16* (2013.01); *C07C 29/48* (2013.01); *C07C 45/40* (2013.01)

(58) Field of Classification Search
CPC ......... C07C 27/12; C07C 27/16; C07C 29/48; C07C 45/40
See application file for complete search history.

(56) References Cited

U.S. PATENT DOCUMENTS

| 3,957,876 A | 5/1976 | Rapoport et al. |
| 4,038,322 A | 7/1977 | De Radzitzky D'Ostrowick et al. |
| 8,801,939 B2 | 8/2014 | Subramaniam et al. |
| 2003/0100805 A1 | 5/2003 | Subramaniam et al. |
| 2012/0037490 A1 | 2/2012 | Kapila et al. |
| 2012/0053354 A1 | 3/2012 | Yoshida |
| 2013/0240781 A1 | 9/2013 | Subramaniam et al. |
| 2014/0065047 A1 | 3/2014 | Hui et al. |
| 2014/0124381 A1 | 5/2014 | Fan |

FOREIGN PATENT DOCUMENTS

DE 19811517 A1 9/1999

OTHER PUBLICATIONS

Bozovic et al., "Conversion of methane to methanol: nickel, palladium, and platinum (d9) cations as catalysts for the oxidation of methane by ozone at room temperature," Chemistry, Oct. 11, 2010, vol. 16, No. 38, pp. 11605-11610.
Lundin et al., "Liquid CO2 as a Safe and Benign Solvent for the Ozonolysis of Fatty Acid Methyl Esters," ACS Sustainable Chem. Eng., 2015, vol. 3, No. 12, pp. 3307-3314.
The International Search Report & Written Opinion dated Oct. 24, 2017 issued in International Patent Application No. PCT/US17/46258, pp. 1-8.

*Primary Examiner* — Sikarl A Witherspoon
(74) *Attorney, Agent, or Firm* — Bell & Manning, LLC (57) ABSTRACT

A process for the ozonolysis of an alkane may comprise combining an alkane and ozone in a liquid phase medium comprising $CO_2$ under conditions sufficient to oxidize the alkane to produce one or more non-combustion products. The liquid phase medium may be free of a super acid.

20 Claims, 3 Drawing Sheets

OZONE-FACILITATED SELECTIVE OXIDATION OF ALKANES IN LIQUID CARBON DIOXIDE

CROSS-REFERENCE TO RELATED APPLICATIONS

This application is a National Stage of International Application No. PCT/US2017/046258, filed Aug. 10, 2017, which claims the benefit of U.S. Patent Application No. 62/373,397, filed Aug. 11, 2016 and the benefit of U.S. Patent Application No. 62/408,863, filed Oct. 17, 2016, the contents of which are herein incorporated by reference.

BACKGROUND

The direct and economically viable conversion of methane to liquid products has been a grand challenge for several decades. Various direct conversion techniques such as oxidative coupling using oxygen (Zavyalova, U., et al. (2011). "Statistical analysis of past catalytic data on oxidative methane coupling for new insights into the composition of high-performance catalysts." *Chem Cat Chem* 3: 1935-1947.) or sulfur (Zhu, Q., et al. (2013). "Sulfur as a selective 'soft' oxidant for catalytic methane conversion probed by experiment and theory." *Nature chemistry* 5: 104-109), non-oxidative coupling to yield hydrocarbons and hydrogen (Nahreen, S., et al. (2016). "Catalytic upgrading of methane to higher hydrocarbon in a non-oxidative chemical conversion." *Energy & Fuels*: acs.energyfuels.5b02583), dehydroaromatization (Spivey, J. J. et al. (2014). "Catalytic aromatization of methane." *Chemical Society Reviews* 43: 792-803), cross coupling with other hydrocarbons (Lunsford, J. H. (1995). "The Catalytic Oxidative Coupling of Methane." *Angewandte Chemie International Edition in English* 34: 970-980), partial oxidation to oxygenates, halogenation (Olah, G. A., et al. (1985). *Journal of the American Chemical Society* 107: 7097-7105) and sulfonation (Mukhopadhyay, S. et al. (2003). "Direct sulfonation of methane to methanesulfonic acid with $SO_2$ using Ca salts as promoters." *Journal of the American Chemical Society* 125: 4406-4407) have been investigated in industry and academia. Despite creative advances in various catalytic methods to convert methane to liquid products, almost all the reported concepts suffer from low product yields and/or safety concerns that prevent their practical viability. The only industrial methane conversion process involves an indirect route wherein the methane is first converted to synthesis gas followed by the catalytic conversion of synthesis gas to liquid fuels or chemical precursors. However, the cost of producing syngas is relatively high and must be reduced for the process to compete with those that currently make the same products from petroleum crude.

SUMMARY

Provided herein are processes for the liquid phase oxidative conversion of hydrocarbons. In an embodiment, a process for the ozonolysis of an alkane comprises combining an alkane and ozone in a liquid phase medium comprising $CO_2$ under conditions sufficient to oxidize the alkane to produce one or more non-combustion products. The liquid phase medium may be free of a super acid.

BRIEF DESCRIPTION OF THE DRAWINGS

Illustrative embodiments of the invention will hereafter be described with reference to the accompanying drawings.

DETAILED DESCRIPTION

The present disclosure provides processes for the liquid phase oxidative conversion of hydrocarbons. By "liquid phase" it is meant that the relevant reactions take place in the liquid phase, as further described below. The oxidation reaction is facilitated by an oxidant and in some embodiments, a catalyst. By contrast to conventional methods for oxidative conversion of hydrocarbons (e.g., methane), at least some embodiments of the present disclosure provide much higher product yields and/or selectivity while reducing costs (e.g., by using more readily available and inexpensive reactants) and improving safety (e.g., by reducing flammability concerns).

In embodiments, a process for oxidizing hydrocarbons includes combining a hydrocarbon reactant and an oxidant in a liquid phase medium containing $CO_2$. The process may be carried out in the presence of a catalyst capable of generating an active species derived from the oxidant. However, in other embodiments, a catalyst is not used. The process takes place under conditions which are sufficient to oxidize the hydrocarbon reactant and, if a catalyst is present, to generate the active species. The products produced by the oxidation include one or more non-combustion products, i.e., products other than $H_2O$ and $CO_2$.

A variety of hydrocarbon reactants may be used. Illustrative hydrocarbon reactants include alkanes. The alkanes may be linear, branched, or cyclic. The alkanes may include various numbers of carbons, e.g., one, two, three, four, five, etc. Alkanes including from one to five carbons (i.e., C1-C5 alkanes) may be referred to herein as "light alkanes." In embodiments, the alkane is a C1-C10 alkane, a C1-C8 alkane, a C1-C6 alkane, or a C1-C5 alkane. Specific illustrative alkanes include methane, ethane, propane, butane, dimethyl propane, heptane, iso-octane and cyclohexane. Combinations of different types of hydrocarbons may be used. The hydrocarbon reactant may be provided pure or in a mixture, e.g., as a gas mixture.

A variety of oxidants may be used. Illustrative oxidants include oxidants which are in their gaseous form at room temperature and atmospheric pressure. Oxidants such as ozone ($O_3$) and nitrous oxide ($N_2O$) may be used. Combinations of different types of oxidants may be used. The oxidant may be provided as a gas mixture, e.g., $O_3$ in $O_2$ or $O_3$ in air.

When using a catalyst, a variety of catalysts may be used, provided the catalyst is capable of generating an active species derived from the oxidant. The active species may be formed on the surface of the catalyst. The active species may be formed by decomposing the selected oxidant. For example, a catalyst which catalyzes the decomposition of ozone according to the scheme below $O_3 \rightarrow O_2 + O$ (activated)

may be used. Here, the activated oxygen is the active species. The activated oxygen may be an oxygen atom covalently bound to the surface of the catalyst. A catalyst which catalyzes the decomposition of nitrous oxide according to the scheme below $N_2O \rightarrow N_2 + O$ (activated or anion)

may be used. Here the activated oxygen (described above) or oxygen anion is the active species. Combinations of different types of catalysts may be used.

The catalyst may contain transition metals such as a first row transition metal (e.g., Fe, Ni) or a platinum group metal, e.g. Pd. The catalysts may be supported transition metal catalysts in which the selected transition metals are incorporated into a metal oxide substrate, e.g., an oxide of aluminum, silicon, titanium, magnesium, etc. Illustrative metal oxide substrates include silicate and zeolite. Mesoporous silicates such as KIT-5, KIT-6, SBA-16, TUD-1 may be used. Methods of incorporating transition metals into such substrates are known, such as techniques based on wet impregnation and strong electrostatic absorption. (See, e.g., Ramanathan, A., et al. (2014). "Niobium incorporated mesoporous silicate, Nb-KIT-6: Synthesis and characterization." *Microporous and Mesoporous Materials* 190: 240-247; Ramanathan, A., et al. (2013). "Tungsten-incorporated cage-type mesoporous silicate: W-KIT-5." *Microporous and Mesoporous Materials* 175: 43-49; Ramanathan, A., et al. (2015). "Facile Styrene Epoxidation with $H_2O_2$ over Novel Niobium Containing Cage Type Mesoporous Silicate, Nb-KIT-5." *Topics in Catalysis* 58(4): 314-324; Ramanathan, A., et al. (2012). "Direct incorporation of tungsten into ultra-large-pore three-dimensional mesoporous silicate framework: W-KIT-6." *Journal of Porous Materials* 19(6): 961-968; Ramanathan, A., et al. (2013). "Synthesis and characterization of Zirconium incorporated ultra large pore mesoporous silicate, Zr-KIT-6." *Microporous and Mesoporous Materials* 167: 207-212; Ramanathan, A., et al. (2015). "Novel zirconium containing cage type silicate (Zr-KIT-5): An efficient Friedel-Crafts alkylation catalyst." *Chemical Engineering Journal* 278: 113-121; Ramanathan, A., et al. (2015). "Comparative Study of Nb-Incorporated Cubic Mesoporous Silicates as Epoxidation Catalysts." *Industrial & Engineering Chemistry Research* 54(16): 4236-4242; Srinivasan, V. V., et al. (2015). "Potential applications of Zr-KIT-5: Hantzsch reaction, Meerwein-Ponndorf-Verley (MPV) reduction of 4-tert-butylcyclohexanone, and Prins reaction of citronellal." *Research on Chemical Intermediates*; Pan, Q., et al. (2013). "Synthesis and Dehydration Activity of Novel Lewis Acidic Ordered Mesoporous Silicate: Zr-KIT-6." *Industrial & Engineering Chemistry Research* 52(44): 15481-15487; Pan, Q., et al. (2014). "Intrinsic Kinetics of Ethanol Dehydration Over Lewis Acidic Ordered Mesoporous Silicate, Zr-KIT-6." *Topics in Catalysis* 57(17-20): 1407-1411; Yan, W., et al. (2014). "Towards highly selective ethylene epoxidation catalysts using hydrogen peroxide and tungsten- or niobium-incorporated mesoporous silicate (KIT-6)." *Catalysis Science & Technology* 4(12): 4433-4439; Yan, W., et al. (2016). "Mechanistic insights for enhancing activity and stability of Nb-incorporated silicates for selective ethylene epoxidation." *Journal of Catalysis* 336: 75-84; Maheswari, R., et al. (2014). "Synthesis, Characterization, and Epoxidation Activity of Tungsten-Incorporated SBA-16 (W-SBA-16)." *Industrial & Engineering Chemistry Research* 53(49): 18833-18839; Munnik, P., et al. (2015). "Recent Developments in the Synthesis of Supported Catalysts." *Chemical Reviews* 115(14): 6687-6718, each of which is hereby incorporated by reference in its entirety. Metalloporphyrin catalysts may also be used (Mang, S., et al. (2000). "Copolymerization of $CO_2$ and 1,2-Cyclohexene Oxide Using a $CO_2$-Soluble Chromium Porphyrin Catalyst." *Macromolecules* 33: 303-308).

The catalyst may be selected to maximize the decomposition of the oxidant as well as to maximize the formation of transition metal-oxygen bonds (also referred to as metal oxo species) e.g., when using the supported transition metal catalysts described above. Catalytic activity may be evaluated via UV/visible spectrophotometry, e.g., by using an Ocean Optics UV/Visible spectrophotometer equipped with fiber optic light paths to measure the decrease in the electronic absorptions of ozone at ca. 254 nm and 590 nm. Molar extinction coefficients for ozone dissolved in liquid $CO_2$ have been previously measured (Lundin, M. D., et al. (2015) "Liquid $CO_2$ as a Safe and Benign Solvent for the Ozonolysis of Fatty Acid Methyl Esters." *ACS Sustainable Chemistry and Engineering*.), thereby enabling accurate quantification of the amount of ozone in solution. Complementary in situ FTIR measurements of the catalyst suspensions may be collected using a high pressure reactor fitted with a Mettler Toledo ReactIR™ attenuated total reflectance (ATR) spectrometer. Modifications to the coordination environment of the transition metal atoms in the catalysts will result in changes to their infrared spectra. Additional confirmation of the formation of the activated catalysts, and the bound substrates, may be obtained with this technique.

As described above, the oxidation reaction is carried out in a liquid phase medium containing $CO_2$, e.g., liquid $CO_2$. The liquid phase medium acts as an inert solvent for the hydrocarbon reactant and the oxidant. The catalyst, if present, may either be dissolved or suspended in the liquid $CO_2$ medium. The oxidation reaction, which takes place in the liquid phase medium, may involve the decomposition of the oxidant, e.g., the decomposition of $O_3$ on the catalyst to activated oxygen or the decomposition of $N_2O$ on the catalyst to activated oxygen or oxygen anion. The oxidation reaction involves the oxidation of the hydrocarbon reactant, e.g., the reaction of activated oxygen or oxygen anion with the hydrocarbon reactant (e.g., methane) to produce a hydrocarbon radical (e.g., methyl radical) and ultimately products (e.g., oxygenated products such as methanol, formaldehyde, carbon monoxide). In the absence of a catalyst, the oxidation reaction may involve the insertion of the oxidant (e.g., ozone) into a CH bond of hydrocarbon reactant to form a hydrotrioxide species which dissociates to form products. However, this mechanism is not meant to be limiting. The particular products produced by the oxidation reaction depend upon the selected hydrocarbon as well as the presence/absence of a catalyst. Possible products as derived from possible alkanes are shown in Table 1, below. Each of these possible products is a non-combustion product, i.e., a product other than $H_2O$ and $CO_2$. Neither the alkane nor the potential oxidation products are meant to be limiting.

TABLE 1

Alkanes and their potential oxidation products.

| Alkane | Potential Oxidation Products |
|---|---|
| methane | Methanol, fomaldehyde |
| ethane | Ethanol, acetic acid, formaldehyde, acetaldehyde |
| propane | Formaldehyde, methanol, acetaldehyde, oxirane, acrolein, oxetane, 2-propen-1-ol, acetone, propanal, methyloxirane, iso-propanol, n-propanol, acetic acid, 1-hydroxy-2-propanone, propyl-hydroperoxide isomers |
| n-butane | Tertiary butyl hydroperoxide (TBHP), tertiary butyl alcohol (TBA), di tertiary butyl |

TABLE 1-continued

Alkanes and their potential oxidation products.

| Alkane | Potential Oxidation Products |
|---|---|
| | peroxide (DTBP), methanol, 2-propanol, isobutanol, isobutanal, propanone, formaldehyde, isopentane |
| dimethyl propane | 2,2-bis(hydroxymethyl)malonaldehyde, 2-hydroxyethane-1,1,1-tricarbaldehyde, methanetetracarbaldehyde, 3-hydroxy-2,2-bis(hydroxymethyl)propanal, 3-hydroxy-2-(hydroxymethyl)-2-methylpropanal, ethane-1,1,1-tricarbaldehyde, 2,2-bis(hydroxymethyl)propane-1,3-diol, 2-(hydroxymethyl)-2-methylpropane-1,3-diol, 2-(hydroxymethyl)-2-methylmalonaldehyde, 2,2-dimethylmalonaldehyde, 3-hydroxy-2,2-dimethylpropanal, 2,2-dimethylpropane-1,3-diol, 2,2-dimethyl-1-propanol, 2,2-dimethylpropanal |
| n-heptane | 4-heptanone, 3-heptanone, 2-heptanone |
| iso-octane | 2,2,4-trimethylpentane-5-one |
| cyclohexane | Cyclohexanone, cyclohexanol |

The oxidation reaction of the present disclosure is in direct contrast to oxidation reactions carried out in the gas phase, e.g., Božović, A., et al. (2010). "Conversion of Methane to Methanol: Nickel, Palladium, and Platinum (d9) Cations as Catalysts for the Oxidation of Methane by Ozone at Room Temperature." *Chemistry—A European Journal* 16: 11605-11610. In addition, the prior art reaction was performed under vacuum conditions with very low concentrations of the reactants (methane and ozone) to avoid flammability/explosion hazards. In sharp contrast, the processes of the present disclosure may be carried out in liquid $CO_2$ permitting the safe use of higher concentrations of methane and ozone at above-ambient pressures. In addition, liquid $CO_2$ is a flame retardant.

The oxidation reaction of the present disclosure is further distinguished from the ozonolysis of alkanes, e.g., methane, in super acid media as suggested in U.S. Pat. No. 8,801,939. By contrast, the present processes do not involve the use of a super acid, e.g., an acid with an acidity greater than 100% pure sulfuric acid (e.g., $SbF_6H$) as a solvent or a reactant. However, in embodiments, certain super acids may be used in the present processes as a catalyst capable of facilitating the decomposition of the oxidant, e.g., ozone. Nevertheless, in embodiments, the present processes make use of liquid phase media free of a super acid.

It is also noted that ozonolysis of alkenes differs significantly from the ozonolysis of alkanes. Alkene ozonolysis proceeds via the Criegee mechanism in which ozone forms a five membered primary ozonide via 1,3-cycloaddition of the ozone molecule to the alkene. The unstable primary ozonide rapidly dissociates to form a carbonyl oxide species and either an aldehyde or ketone. These two species recombine to yield a secondary ozonide that is quite stable even in the presence of ozone. By contrast, the chemistry of alkane ozonolysis does not involve the Criegee mechanism. Further, the intermediate products of alkane oxidation are generally much more reactive towards ozone than their starting compounds. A strong oxidant like ozone has the potential to completely oxidize alkanes to carbon dioxide and water. In fact, ozone is widely used in water treatment precisely because of its ability to perform total oxidation of organic molecules. However, the present invention is based, at least in part, on the inventors' discovery of processes which operate at close to ambient temperatures and are capable of providing high yields of desirable non-combustion products (see Table 1) and/or high selectivity despite the susceptibility of the intermediate products for further reaction with ozone.

The processes of the present disclosure may take place under conditions which are sufficient to oxidize the hydrocarbon reactant and, if a catalyst is used, to decompose the oxidant on the catalyst. These conditions include the temperature, the pressure, and the relative amounts of the hydrocarbon reactant, oxidant, and $CO_2$. The temperature and pressure may be selected to liquefy $CO_2$ (i.e., to provide liquid $CO_2$ as the liquid phase medium) as well as to adjust the concentration of the oxidant and the hydrocarbon reactant in the liquid phase medium (e.g., ozone and hydrocarbon solubilities in liquid $CO_2$ can be tuned by the appropriate selection of temperature and pressure). The temperature of the liquid phase medium may be in the range of from about −100° C. to about 100° C. This includes embodiments in which the temperature is in the range of from about −75° C. to about 75° C., from about −60° C. to about 65° C., from about −60° C. to about 55° C., from about −60° C. to about 45° C., or from about −60° C. to about 35° C. This further includes embodiments in which the temperature is no greater than the critical temperature of $CO_2$ (about 31.1° C.). This further includes embodiments in which the temperature is no greater than 25° C., in the range of from about 0° C. to about 25° C., in the range of from about 5° C. to about 25° C., or in the range of from about 5° C. to about 15° C. These temperatures are significantly lower than those used in conventional oxidative conversions of methane. These temperatures also help to either minimize or eliminate deep oxidation products.

The pressure refers to the total pressure of the vapor phase/dense phase present over the liquid phase medium. A pressure in the range of from about 1 bar to about 100 bar may be used. This includes embodiments in which the pressure is in the range of from about 1 bar to about 95 bar, from about 1 bar to about 90 bar, from about 1 bar to about 85 bar, from about 1 bar to about 80 bar, or from about 5 bar to about 75 bar. This further includes embodiments in which the pressure is no greater than the critical pressure of $CO_2$ (about 73.9 bar). These pressures are significantly greater than those used in conventional oxidative conversions of methane.

Figure 1:
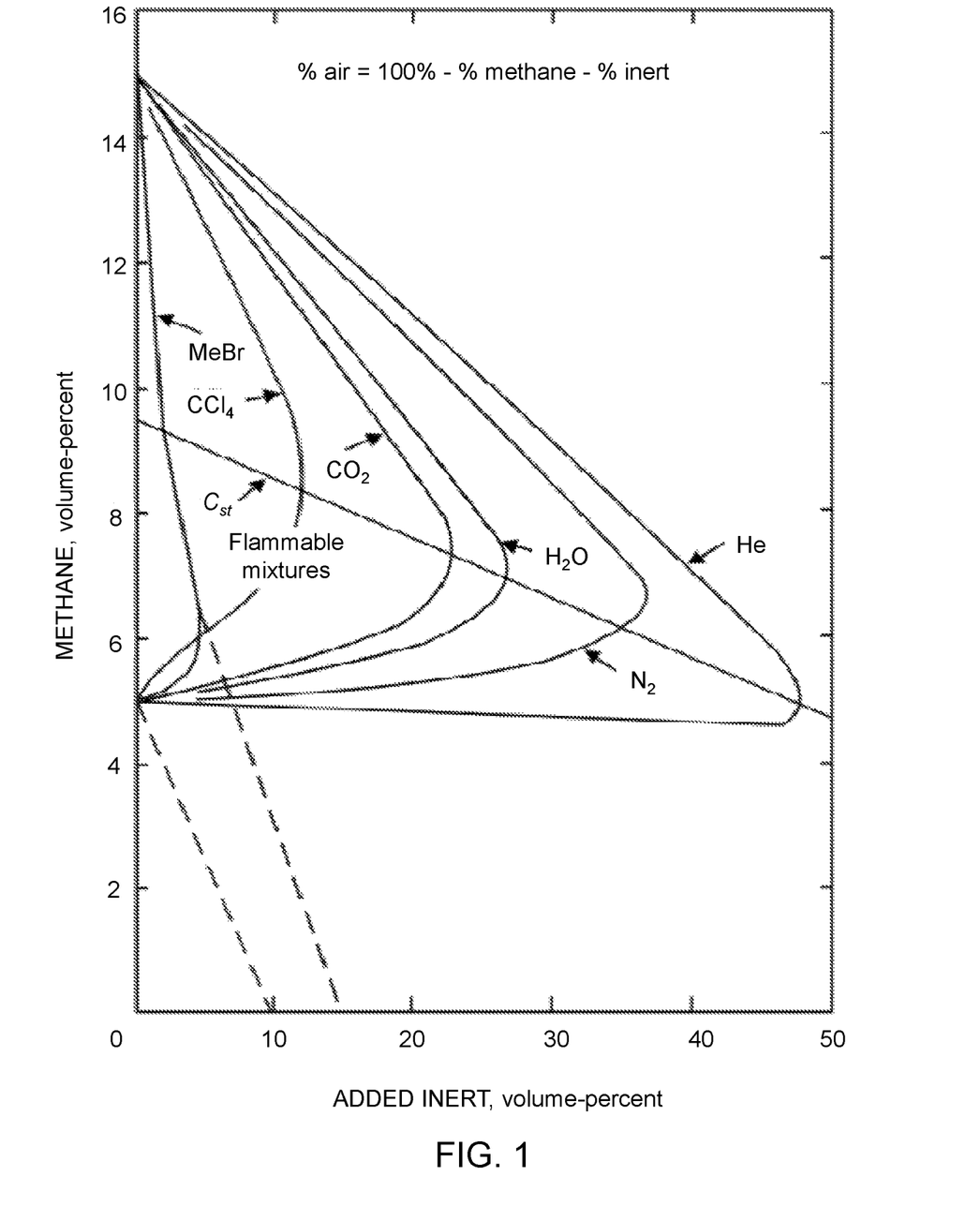
FIG. 1 shows the limits of flammability of various methane-inert-gas-air mixtures at 25° C. and atmospheric pressure.

The relative amounts of the hydrocarbon reactant, oxidant, and $CO_2$ may refer to the amount (in mole %) added to a reaction cell containing the liquid phase medium. The term "added" may refer to a one-time addition in a batch reactor system or a continuous addition in a continuous flow reactor system. The hydrocarbon reactant and the oxidant (e.g., $O_3$ or $N_2O$) may be added in stoichiometrically equivalent amounts. The relative amount of the combined hydrocarbon reactant/oxidant and the $CO_2$ may be selected to achieve desired reaction rates/product yields while also ensuring that the composition of the vapor phase/dense phase over the reaction medium is outside the relevant flammability envelope at the selected temperature and pressure. By way of illustration, the flammability envelope for various methane-inert gas-air mixtures at 25° C. and atmospheric pressure is shown in FIG. 1. This figure shows that the flammability envelope for methane is reduced when $CO_2$ is used as compared to $N_2$, i.e., from 35% (by volume) $N_2$ and 7% methane (remainder air) to about 23% (by volume) $CO_2$ and 7% methane (remainder air). The use of liquid $CO_2$ as the liquid phase medium results in a vapor phase dominated by dense $CO_2$. The amount of combined hydrocarbon reactant/oxidant may be selected so that the concentration of the hydrocarbon reactant/oxidant in the vapor phase is below the lower flammability limit. In embodiments, the combined hydrocarbon reactant/oxidant is added in an amount ranging from about 1 mole % to about 45 mole %, and the $CO_2$ is added in an amount ranging from about 55 mole % to about 99 mole %. This includes embodiments in which the combined hydrocarbon reactant/oxidant is added in an amount ranging from about 10 mole % to about 40 mole %, and the $CO_2$ is added in an amount ranging from about 60 mole % to about 90 mole %. This further includes embodiments in which the combined hydrocarbon reactant/oxidant is added in an amount ranging from about 30 mole % to about 40 mole %, and the $CO_2$ is added in an amount ranging from about 60 mole % to about 70 mole %.

Another condition of the present processes includes the reaction time. Illustrative reaction times include less than about 60 minutes, less than about 30 minutes, less than about 25 minutes, as well as those in the range of from about 0.1 minutes to about 40 minutes, from about 0.5 minutes to about 25 minutes, or from about 1 minute to about 25 minutes.

Other advantages of using liquid $CO_2$ beyond shrinking the flammability envelope are as follows. Liquid $CO_2$ can solubilize ozone and reactant in high concentrations to alleviate reactant starvation in the liquid phase medium containing the catalyst. This facilitates facile catalytic $O_3$ decomposition and relatively facile hydrocarbon oxidation to oxygenated products. In addition, by controlling the hydrocarbon addition, the liquid $CO_2$ can be used as an effect heat sink to absorb the heat of reaction and provide evaporative cooling, thus making the system inherently stable. For example, for a reactor cell with an internal volume of 13.85 $cm^3$, the heat of combustion of 13.04 $cm^3$ of $CH_4$ at a partial pressure of 0.55 bar would be offset by the heat of vaporization of 0.81 $cm^3$ $CO_{2(l)}$, presuming a temperature of $-1.6°$ C. Additional $CO_2$ beyond this quantity would provide a further measure of safety.

The processes of the present disclosure may be characterized by the yield (in g/hr) of a particular product at the selected conditions, e.g., when using continuous flow reactors. By way of illustration, in embodiments in which the hydrocarbon reactant is methane, the process may be characterized by the yield of methanol at the selected conditions. In embodiments, the yield of methanol may be at least 100 g/hr. This includes embodiments in which the yield of methanol is at least 150 g/hr, at least 200 g/hr, or at least 250 g/hr. This is orders of magnitude greater than the millimolar quantities reported in the absence of $CO_2$ (Knops-Gerrits, P. P. et al. (2001). "Methane partial oxidation in iron zeolites: Theory versus experiment." *Journal of Molecular Catalysis A: Chemical* 166: 135-145.)

The processes of the present disclosure may be characterized by the conversion (%) of hydrocarbon reactant to product at the selected conditions, e.g., when using batch reactors. By conversion, it is meant ((moles of total product)/(moles of hydrocarbon reactant fed))*100. The conversion may be at least 50%, at least 60%, at least 70%, at least 80%, at least 90%, or at least 95%. By minimizing combustion products, the obtained products are mostly oxygenated products as shown in Table 1. Hence the yield of the oxygenated products is approximately equal to the total conversion.

The processes of the present disclosure may be characterized by the selectivity for a particular product. By selectivity, it is meant ((moles of particular product)/(total moles of products obtained))*100. Depending upon the hydrocarbon reactant, the selectivity of a single desirable product may be quite high, e.g., at least 70%, at least 80%, at least 90%, at least 95%. By way of illustration, the oxidation of cyclohexane using the processes of the present disclosure may produce cyclohexanone with a selectivity of at least 90%, at least 95%, at least 97%, or even 100%. In other cases, the selectivity for multiple desirable products may be substantially equal. By way of illustration, the oxidation of n-heptane using the processes of the present disclosure may produce 4-heptanone, 3-heptanone, and 2-heptanone, with substantially equal selectivities, e.g., about 33%. By "substantially equal" it is meant that the selectivities are within ±15% of each other.

The yield (%) of a particular product is defined as the conversion (%) multiplied by the selectivity (%) towards the particular product. The conversions, yields and selectivities may be reported with reference to the conditions (e.g., one or more of the temperature, the pressure, the relative amounts of the hydrocarbon reactant, oxidant, and $CO_2$, and the reaction time) used in the process.

The processes of the present disclosure may be characterized by the substantial absence of combustion products, i.e., $H_2O$ and $CO_2$. That is, the process produces substantially no $H_2O$ and $CO_2$. By "substantial absence" and "substantially no" it is meant that the amount of $H_2O$ and/or $CO_2$ is less than 5%, less than 3% or less than 1%. By minimizing the combustion products, the obtained products are mostly oxygenated in nature as shown in Table 1. In other words, the selectivity toward the oxygenated products is about 100%. Hence the total yield of the oxygenated products is about equal to the total conversion.

Figure 2:
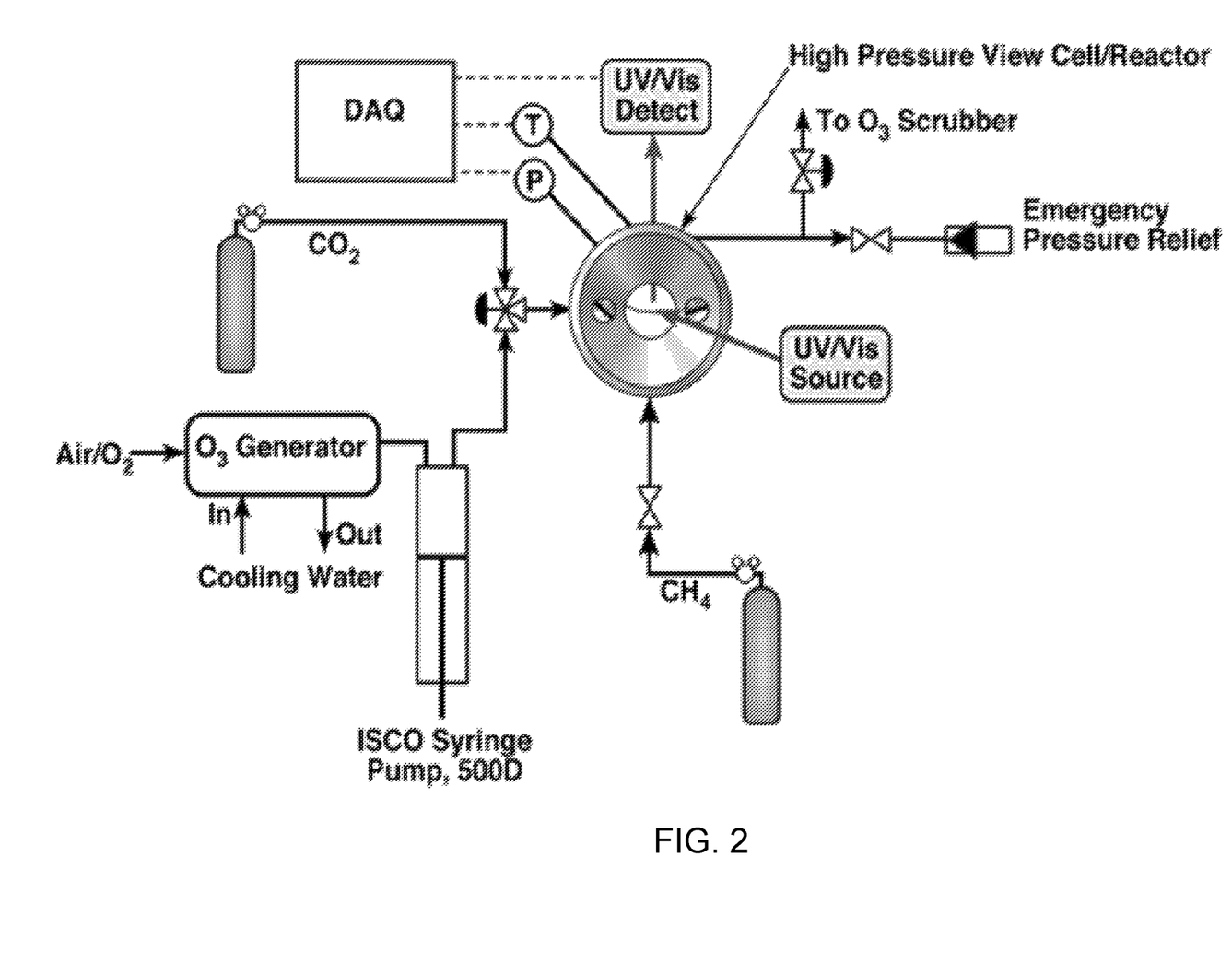
FIG. 2 is a schematic of a batch view cell reactor which may be used for carrying out the processes of the present disclosure.

The processes of the present disclosure may be carried out in a variety of reactor systems, including batch reactor systems and continuous flow reactor systems. FIG. 2 shows a schematic of an illustrative batch reactor system which may be used. In an illustrative process, if utilized, the catalyst is introduced into a titanium view cell reactor. Liquid $CO_2$ is introduced from a Matheson supplied tank fitted with a dip-tube. A PraxAir Unizone™ LO ozone generator is used to produce ozone from Matheson supplied Extra-Dry Oxygen and a Teledyne ISCO 500D syringe pump is used to compress the $O_3/O_2$ mixture into the view cell. The titanium view cell has pressure monitoring via a pressure transducer and temperature monitoring via type K thermocouple. Safety precautions include incorporation of multiple pressure relief devices, the placement of the reaction vessel in a fume hood, and limiting the amount of organic material available for potential combustion. After loading $CO_2$, a small amount of hydrocarbon reactant (e.g., $CH_4$) is added before adding the air/ozone mixture to initiate the oxidation reaction. This order of adding reactants, along with the presence of $CO_2$ as an added inert, helps to ensure that the vapor phase composition remains outside the flammability envelope for the entirety of the experiment, regardless of the total pressure.

Ozone concentration within the cell is measured using an Ocean Optics UV/Visible spectrophotometer equipped with fiber optic light paths. Several methods of product analysis may be used. Infrared spectra of the reaction solutions may be collected using a high pressure reactor fitted with a Mettler Toledo ReactIR™ spectrometer. Partial oxidation products will contain O—H and C—O bonds which have strong IR signals. Liquid samples of known volume may be collected from the reactor and expanded into a pressure vessel containing a known volume of solvent which may be analyzed for oxygenated products using conventional GC, GC/MS and HPLC techniques. Gas-phase samples may be analyzed for volatile hydrocarbons and combustion products using a GC equipped with a cryogenic oven and TCD detector.

Figure 3:
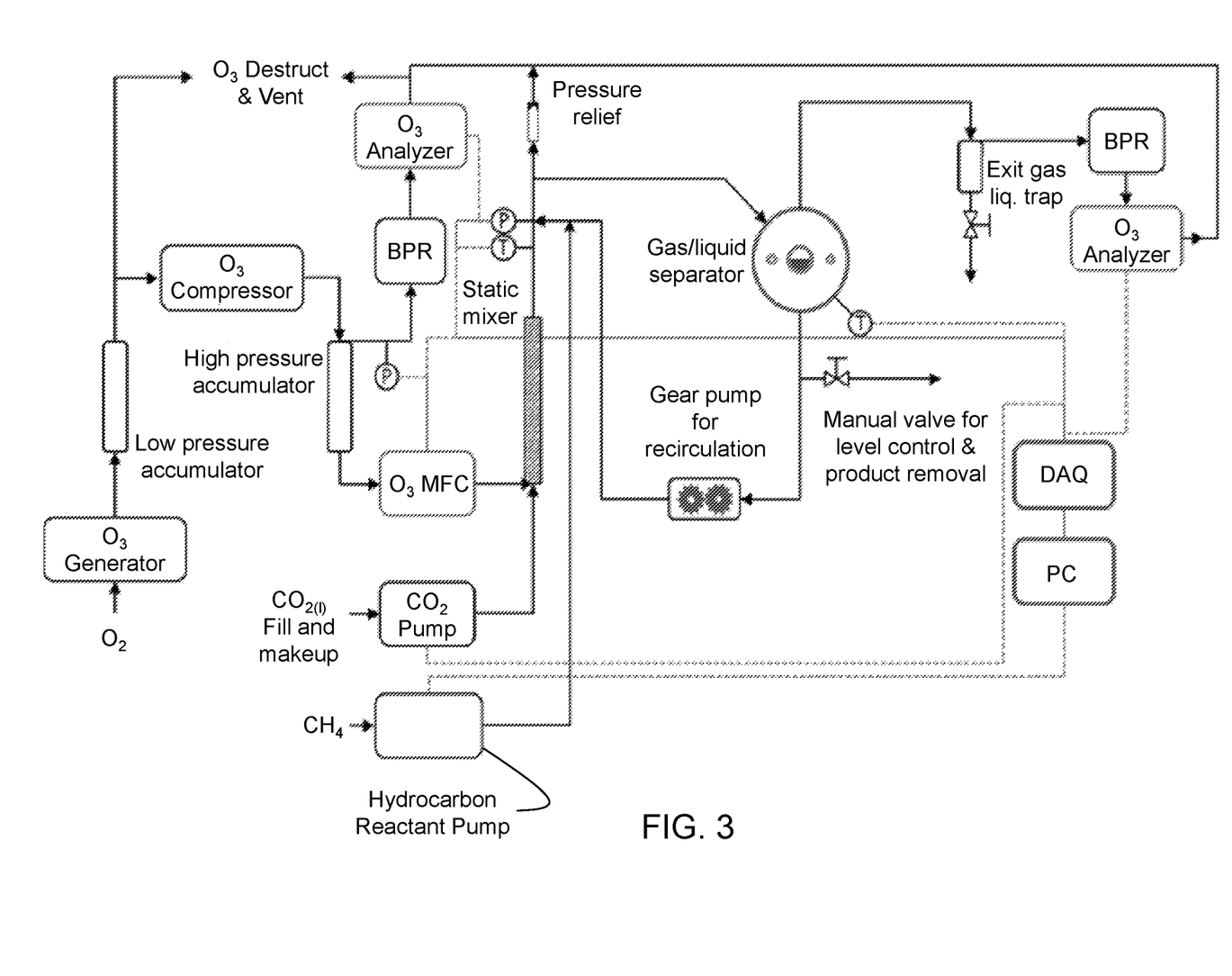
FIG. 3 is a schematic of a continuous flow reactor which may be used for carrying out the processes of the present disclosure.

FIG. 3 shows a schematic of an illustrative continuous flow reactor system which may be used to carry out the processes of the present disclosure. This system advances on batch operation by implementing a dual ISCO 500D syringe pump for continuous supply of liquid $CO_2$ at high pressure, a RIX MicroBoost oxygen compressor retrofitted for operation with $O_3$ coupled to a Brooks mass flow controller (MFC) for metering $O_2/O_3$. Back-pressure regulators (BPR) are used to control system pressure and automated control of flow-rates and performance monitoring is provided via a connected PC and National Instruments hardware. Separation of the liquid phase products from the reaction mixture is achieved by pressure reduction in the effluent stream.

Other details about reactor systems and conditions are described in the Examples, below.

EXAMPLES

A series of reactions were carried out using a batch reactor, similar to that shown in FIG. 2. Some reactions were carried out without a catalyst. Using the reaction with cyclohexane as an illustrative reaction, 100 µL of cyclohexane was introduced into the titanium view cell with a reactor volume of 14 ml. The titanium view cell had pressure monitoring via a pressure transducer and temperature monitoring via type K thermocouple. Safety precautions included incorporation of multiple pressure relief devices, the placement of the reaction vessel in a fume hood, and limiting the amount of organic material available for potential combustion. A thermal jacket surrounding the reactor was used in conjunction with a circulating water bath to maintain the temperature of the reactor at ca. 22° C. After the addition of substrate (cyclohexane), the reactor was sealed and liquid $CO_2$ (ca. 10 ml, 875 psi) was introduced from a Matheson supplied tank fitted with a dip-tube. A PraxAir Unizone™ LO ozone generator was used to produce ozone from dry air ($[O_3]$ in $O_3$/air mixture=1.5 wt %). Once the reactor had reached thermal equilibrium, a Teledyne ISCO 500D syringe pump was used to compress the $O_3$/air mixture into the view cell ($pO_3$/air mixture=475 psi). After addition of the ozone the reaction was allowed to proceed for 20 minutes, after which the pressure was released by slowly venting the gas from the reactor through a trap cooled to 0° C. A gas sample was collected and analyzed using a gas analysis method on a GC fitted with a TCD detector. The reactor and vent trap were then washed with diethyl ether to collect liquid products which were analyzed using GC.

Other reactions were carried out using a similar method, but in the presence of a catalyst. Using the reaction with n-heptane as an illustrative reaction, 17 mg of Pd KIT-6 catalyst was added to the reactor as described previously, followed by the addition of 102 µL n-heptane. The reactor temperature was set to ca. 11.5° C. and the reactor was then sealed and liquid $CO_2$ (ca. 10.6 ml, 640 psi) was introduced from a Matheson supplied tank fitted with a dip-tube. The ISCO pump was used to pump an $O_3$/air mixture ($[O_3]$ in $O_3$/air mixture=1.5 wt %) into the view cell ($pO_3$/air mixture=400 psi). After addition of the ozone, the reaction was allowed to proceed for 20 minutes, after which the pressure was released by slowly venting the gas from the reactor through a trap cooled to 0° C. A gas sample was collected and analyzed using a gas analysis method on a GC fitted with a TCD detector. The reactor and vent trap were then washed with diethyl ether to collect liquid products which were analyzed using GC.

Table 2, below, summarizes the experiments conducted using a variety of alkanes under a variety of conditions.

TABLE 2

Results from ozone-facilitated oxidation of various alkanes using a batch reactor.

| Substrate | Products | Selectivities (%) |
|---|---|---|
| Experimental conditions: Without catalyst. T = 10.1° C., $p_{methane}$ = 8 psi, $pCO_2$ = 638 psi (liquid volume 10.6 ml), $pO_3$/Air = 354 psi, ($[O_3]$ in $O_3$/Air mixture = 1.5 wt %); t = 20 min. With catalyst. 8 mg Pd KIT-6 catalyst, T = 10.2° C., $p_{methane}$ = 8 psi, $pCO_2$ = 634 psi (liquid volume 10.6 ml), $pO_3$/Air = 378 psi, ($[O_3]$ in $O_3$/Air mixture = 1.5 wt %); t = 20 min. | | |
| Methane | Methanol | None observed without catalyst Observed with catalyst but not quantified |
| | Formaldehyde | Trace amounts observed without and with catalyst, but not quantified |
| Experimental Conditions: Without catalyst. 100 µL substrate, T = 11.4° C., $pCO_2$ = 643 psi (liquid volume 10.6 ml), $pO_3$/Air = 392 psi, ($[O_3]$ in $O_3$/Air mixture = 1.5 wt %); t = 20.5 min. With 17 mg Pd KIT-6 catalyst, 102 µL substrate, T = 11.5° C., $pCO_2$ = 640 psi (liquid volume 10.6 ml), $pO_3$/Air = 400 psi, ($[O_3]$ in $O_3$/Air mixture = 1.5 wt %); t = 20.5 min. | | |
| n-heptane | 4-heptanone | 30.4% without catalyst 24.6% with catalyst |
| | 3-heptanone | 38.5% without catalyst 36.9% with catalyst |
| | 2-heptanone | 31.1% without catalyst 38.5% with catalyst |
| Experimental Conditions: Without catalyst. 102 µL substrate, T = 8.1° C., $pCO_2$ = 670 psi, $pO_3$/Air = 430 psi, ($[O_3]$ in $O_3$/Air mixture = 1.5 wt %; t = 24 min With catalyst. 17 mg Pd KIT-6 catalyst, 100 µL substrate, T = 9.2° C., $pCO_2$ = 704 psi, $pO_3$/Air = 300 psi, ($[O_3]$ in $O_3$/Air mixture = 1.5 wt %); t = 25 min | | |
| Iso-octane | 2,2,4-trimethylpentane-5-one | This product + ca. 12 other oxygenated products, not quantified. |
| Experimental Conditions: Without catalyst. 100 µL substrate, T = 22.0° C., $pCO_2$ = 875 psi, $pO_3$/Air = 475 psi, ($[O_3]$ in $O_3$/Air mixture = 1.5 wt %) | | |
| Cyclohexane | cyclohexanone | 97% |
| | cyclohexanol | 3% |

As shown in Table 2, runs for ozone-facilitated methane activation in liquid $CO_2$ revealed conclusive and repeatable evidence of methanol formation in the presence of a supported Pd catalyst. However, either in the absence of catalyst or in the presence of the catalyst and $O_2$ or in the presence of $O_2$ alone, no measurable quantities of methanol were observed. It is particularly noteworthy that even though the methane concentrations used were small for safety reasons, they are still orders of magnitude greater than what is reported in the literature at vacuum conditions. (Knopps-Gerrits, P. P. and W. A. Goddard (2001). "Methane partial oxidation in iron zeolites: Theory versus experiment." *Journal of Molecular Catalysis A: Chemical* 166: 135-145.) The precise amount of methanol formed was not quantified. Further, the existence of combustion products ($H_2O$, $CO_2$) was not assessed since they are formed in amounts too small for reliable measurement, especially in a huge background of $CO_2$. If indeed combustion products were formed in appreciable amounts, a measurable pressure increase would have been observed. However, no such pressure increase was observed.

As shown in Table 2, higher alkanes such as n-heptane, iso-octane and cyclohexane were also investigated. Higher alkanes tend to be increasingly more soluble in liquid $CO_2$ as chain length increases. As such, higher substrate concentrations may be used compared to methane while still avoiding vapor phase flammability. The use of higher concentrations allows easier product quantification. As seen from Table 2, n-heptane produces significant amounts of oxygenates corresponding to the activation of each of the internal C—H bonds. Similarly, iso-octane also produces significant quantities of the corresponding ketone and other oxygenated products. Cyclohexane was also investigated as a substrate. Nearly total selectivity toward cyclohexanone was measured with approximately 50% conversion of the cyclohexane in approximately 20 minutes. This result is extremely significant in the context of an environmentally benign alternative for producing the adipic acid intermediate. The current industrial process for making adipic acid poses significant environmental concerns stemming from the use of nitric acid as an oxidant, which results in the production of significant $N_2O$ emissions that require safe disposal. (Gürsel, I. V., Q. Wang, T. Noël and V. Hessel (2012), "Process-Design Intensification—Direct Synthesis of Adipic Acid in Flow," *Chemical Engineering Transactions*, 29: 565-571.)

A continuous reactor was also used to carry out the continuous ozonolysis of cyclohexane in liquid $CO_2$, using a continuous flow reactor similar to that shown in FIG. 3. The continuous flow reactor advances on the batch operation by implementing a dual ISCO 500D syringe pump for continuous supply of liquid $CO_2$ at high pressure and a RIX MicroBoost oxygen compressor retrofitted for operation with $O_3$ coupled to a Brooks mass flow controller for metering $O_2/O_3$. Back-pressure regulators control system pressure and automated control of flow-rates and performance monitoring is provided via a connected PC and National Instruments hardware. Separation of the liquid phase oxidation products from the reaction mixture is achieved by pressure reduction in the effluent stream. The separated liquid phase is analyzed by a complement of analytical techniques as explained above with respect to the batch reactor.

Ozone is temporarily held in a 300 ml 316 stainless steel pressure vessel. The majority of this ozone is fed to a compressor, while the remainder is vented after being routed through an ozone destructor. The compressor used is a RIX Microboost oxygen compressor retrofitted in-house for ozone compatibility with 316 SS and Kalrez perfluoroelastomer components to tolerate high ozone concentrations and cooled to minimize adverse impacts of heat buildup on ozone stability. The compressed oxygen/ozone mixture is pumped to a high pressure reservoir before being fed into the reactor by a Brooks SLA mass flow controller. Any excess $O_3/O_2$ mixture is vented through a back-pressure regulator to the ozone destruction unit after passing through a Teledyne API model 452 ozone analyzer, the data obtained from which is used to determine the quality of ozone feed to the reactor.

Liquid $CO_2$ pumped by a Teledyne ISCO 500D dual syringe pump is mixed with the ozone/oxygen mixture entering the reactor via an Omega FMX 8400 series static mixer. Downstream of the static mixer, the substrate is pumped into the reactor via an additional ISCO pump and contacted with the $O_3$ rich liquid $CO_2$ at a simple mixing point. The resulting gas/liquid stream is directed to a high-pressure view cell where the gas and liquid phases are allowed to separate by gravity. The gas exits through a back pressure regulator to a second Teledyne API model 452 ozone analyzer and then an ozone destruction unit before being vented. The tubing from the mixing point to the view cell (with an effective volume of approximately 0.6 ml) acts as the reactor with the view cell used to separate the vapor and liquid phases. Pressure is measured using Omega PX329 series pressure transducers and temperatures are measured with Omega HTQ series type T thermocouples. An external chiller was used to provide the cooling needed for the lines and devices. All data were recorded every 5 seconds by a National Instruments FieldPoint data acquisition system (DAQ) and a suitably interfaced computer.

Startup of the ozonolysis reactor is achieved by first chilling the reactor to the typical operating temperature of 0° C. before introducing liquid $CO_2$. After the liquid $CO_2$ level had stabilized, compressed $O_3$ was gradually introduced with the feed rate ramped up to the steady state flow-rate of 2000 std. ml $min^{-1}$. Following reactor pressurization to the operating pressure of 70 bar, additional $CO_2$ was added as necessary to maintain a constant liquid level. Upon achieving the desired operating temperature and pressure, control of the feed flow rates was switched from manual control to automatic. The flow-rates of the reactants are controlled based on user input of the desired alkane/$O_3$ ratio and the alkane feed rate. The mass flow rate of $O_2/O_3$ fed to the reactor (controlled by a Brooks MFC) is calculated based on the desired alkane/$O_3$ ratio and the concentration of ozone in the feed gas (measured by the ozone analyzer). Given that the concentration of $O_3$ produced by the generator varied between 3.7-4.3 mol %, the substrate feed rate is independently controlled based on measurement of the $O_3$ concentration exiting the compressor to maintain a constant alkane/$O_3$ ratio in the feed.

The excess $O_3$ and $O_2$ gases that are not absorbed in liquid $CO_2$ pass through the reactor in the vapor phase. In addition, the vapor phase also contains $CO_2$ that is continuously stripped from the liquid phase by the gas stream passing through the reactor. Vapor-liquid equilibrium modeling of the $CO_2+O_2$ binary system is used to estimate the amount of $CO_2$ stripped from the liquid phase at the system temperatures and pressures, and to estimate the required makeup $CO_2$ flow rates at steady state (Fredenslund A. S. (1970), "Gas-liquid equilibrium of the oxygen-carbon dioxide system," *J. Chem. Eng. Data.* 15(1):17-22.)

Several measures are incorporated in the reactor setup. First, ozone is used as a limiting reactant to limit the rate and extent of reaction. A safety rupture disk is provided in the reactor for pressure relief. An automated shut-down procedure is initiated in the event of pressure and/or temperature excursions beyond specified limits. The steps include shutting off the substrate and ozone flows while evacuating the reactor with flowing $CO_2$.

Using this procedure, the continuous ozonolysis of cyclohexane in liquid $CO_2$ was carried out. The results are shown in Table 3. There was no evidence of water as a combustion product.

TABLE 3

Results from ozone-facilitated oxidation of cyclohexane using a continuous flow reactor. Operating conditions: P = 70 bar; T = 0° C.; $O_3$:cyclohexane = 1:1; liquid $CO_2$ = 60 vol. % of liquid feed rate; residence time: a few seconds.

| | Sample 1 | Sample 2 |
|---|---|---|
| Yield of: | | |
| Cyclohexanone | 3.46% | 3.14% |
| Cyclohexanol | 0.46% | 0.41% |
| Conversion of: | | |
| Cyclohexane | 3.92% | 3.55% |

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more".

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A process for the ozonolysis of an alkane, the process comprising combining an alkane and ozone in a liquid phase medium comprising $CO_2$ under conditions sufficient to oxidize the alkane to produce one or more non-combustion products, wherein the liquid phase medium is free of a super acid,
  wherein the alkane and the ozone are added in stoichiometrically equivalent amounts, further wherein the combined alkane and ozone is added in an amount ranging from about 1 mole % to about 45 mole %, and the $CO_2$ is added in an amount ranging from about 55 mole % to about 99 mole %.

2. The process of claim 1, wherein the alkane is a C1-C10 alkane.

3. The process of claim 2, wherein the alkane is selected from methane, ethane, propane, iso-butane, dimethyl propane, heptane, iso-octane, cyclohexane, and combinations thereof.

4. The process of claim 2, wherein the alkane is methane and the one or more non-combustion products comprise methanol.

5. A process for the ozonolysis of an alkane, the process comprising combining an alkane and ozone in a liquid phase medium comprising $CO_2$ under conditions sufficient to oxidize the alkane to produce one or more non-combustion products, wherein the liquid phase medium is free of a super acid, wherein the alkane is n-heptane and the one or more non-combustion products comprise 4-heptanone, 3-heptanone, and 2-heptanone or the alkane is cyclohexane and the one or more non-combustion products comprise cyclohexanone and cyclohexanol.

6. The process of claim 1, wherein the liquid phase medium is liquid $CO_2$.

7. The process of claim 1, wherein the process is carried out in the presence of a catalyst capable of generating an active species derived from the ozone and the conditions are sufficient to generate the active species.

8. The process of claim 7, wherein the catalyst is a supported transition metal catalyst comprising transition metals incorporated into a metal oxide substrate, wherein the metal oxide substrate is an oxide of a metal selected from aluminum, silicon, titanium, and magnesium.

9. The process of claim 8, wherein the supported transition metal catalyst comprises Fe, Ni, Pd, or combinations thereof, incorporated into a mesoporous silicate.

10. The process of claim 1, wherein the process produces substantially no $H_2O$ and substantially no $CO_2$.

11. The process of claim 1, wherein the process is carried out at a temperature and pressure selected to liquefy the $CO_2$.

12. The process of claim 11, wherein the process is carried out for a reaction time of no more than about 30 minutes.

13. A process for the ozonolysis of an alkane, the process comprising combining an alkane and ozone in a liquid phase medium comprising $CO_2$ under conditions sufficient to oxidize the alkane to produce one or more non-combustion products, wherein the liquid phase medium is free of a super acid, wherein one of the one or more non-combustion products is produced with a selectivity of at least 95%; or multiple non-combustion products are produced with substantially equal selectivities.

14. The process of claim 1, wherein the alkane is methane and the one or more non-combustion products comprise methanol and the process provides a yield of methanol of at least 100 g/hr.

15. The process of claim 5, wherein the alkane is n-heptane and the one or more non-combustion products comprise 4-heptanone, 3-heptanone, and 2-heptanone and the process provides substantially equal selectivities of 4-heptanone, 3-heptanone, and 2-heptanone.

16. The process of claim 5, wherein the alkane is cyclohexane and the one or more non-combustion products comprise cyclohexanone and the process provides a selectivity of cyclohexanone of at least 95%.

17. The process of claim 16, wherein the process is characterized by a selectivity of cyclohexane toward the one or more non-combustion products of at least 90%.

18. A process for the ozonolysis of an alkane, the process comprising combining an alkane and ozone in a liquid phase medium comprising $CO_2$ under conditions sufficient to oxidize the alkane to produce one or more non-combustion products, wherein the liquid phase medium is free of a super acid and the alkane is not methane.

19. The process of claim 18, wherein the alkane is selected from ethane, propane, iso-butane, dimethyl propane, heptane, iso-octane, cyclohexane, and combinations thereof.

20. A process for the ozonolysis of methane, the process comprising combining methane and ozone in a liquid phase medium comprising $CO_2$ under conditions sufficient to oxidize methane to produce one or more non-combustion products, wherein the liquid phase medium is free of a super acid,
- wherein the process is carried out in the presence of a catalyst capable of generating an active species derived from the ozone and the conditions are sufficient to generate the active species,
- wherein the catalyst is a supported transition metal catalyst comprising Fe, Ni, Pd, or combinations thereof, incorporated into a mesoporous silicate, and
- wherein the process produces substantially no $H_2O$ and substantially no $CO_2$.

* * * * *